(12) United States Patent
Chon et al.

(10) Patent No.: US 10,561,529 B2
(45) Date of Patent: Feb. 18, 2020

(54) SURGICAL HANDPIECE WITH REVERSE FLOW PRIMING

(71) Applicant: Novartis AG, Basel (CH)

(72) Inventors: James Y. Chon, Irvine, CA (US); Robert Stephen Maurer, Jr., Huntington Beach, CA (US); Satish Yalamanchili, Irvine, CA (US)

(73) Assignee: Novartis AG, Basel (CH)

( * ) Notice: Subject to any disclaimer, the term of this patent is extended or adjusted under 35 U.S.C. 154(b) by 110 days.

(21) Appl. No.: 15/864,624

(22) Filed: Jan. 8, 2018

(65) Prior Publication Data

US 2018/0200109 A1    Jul. 19, 2018

Related U.S. Application Data

(60) Provisional application No. 62/447,648, filed on Jan. 18, 2017.

(51) Int. Cl.
*A61F 9/007* (2006.01)
*A61M 1/00* (2006.01)
*A61B 17/32* (2006.01)

(52) U.S. Cl.
CPC ....... *A61F 9/00745* (2013.01); *A61M 1/0064* (2013.01); *A61B 2017/320084* (2013.01)

(58) Field of Classification Search
CPC .............. A61F 9/00745; A61F 9/00736; A61F 9/00754; A61F 9/00763; A61F 9/00781; A61F 9/007; A61F 9/008; A61B 17/22012; A61B 17/320092; A61B 18/1402; A61B 18/24; A61B 17/320068; A61B 17/32002; A61B 17/3203; A61M 1/0058; A61M 1/0031; A61M 1/0064; A61M 1/0084; A61M 3/0258; A61M 3/0283; A61M 3/0279; A61M 1/008; A61M 1/0062; A61N 7/00; A61C 17/0202
USPC .......................................... 604/22; 606/169
See application file for complete search history.

(56) References Cited

U.S. PATENT DOCUMENTS

| | | | |
|---|---|---|---|
| 4,492,574 A | 1/1985 | Warrin et al. | |
| 5,151,083 A * | 9/1992 | Pichler | A61B 17/320068 604/22 |
| 5,211,625 A | 5/1993 | Sakurai et al. | |
| 5,417,654 A | 5/1995 | Kelman | |
| 5,746,713 A | 5/1998 | Hood et al. | |
| 2002/0077585 A1 * | 6/2002 | Sussman | A61F 9/00736 604/22 |

FOREIGN PATENT DOCUMENTS

JP    H08275953 A    10/1996

* cited by examiner

*Primary Examiner* — Manuel A Mendez

(57) ABSTRACT

A method and system provide a surgical handpiece including a housing and a horn. The housing has a retrograde channel and a chamber a therein. The retrograde channel connects an irrigation line and the chamber. The horn is held within the housing such that a portion of the horn resides within the chamber.

11 Claims, 3 Drawing Sheets

SURGICAL HANDPIECE WITH REVERSE FLOW PRIMING

BACKGROUND

FIG. 1 depicts a portion of a conventional ultrasonic handpiece 10 usable in ophthalmic surgery. The ultrasonic handpiece 10 includes a housing 12 and a horn 20 which vibrates ultrasonically in the housing 12. The housing 12 includes an irrigation line 14, a channel 16 and a chamber 18 through which fluid may flow. The irrigation line 14 runs along the axis of the handpiece 10 and may be formed of a separate component. The chamber 18 is centrally located. The horn 20 extends through the chamber 18. The horn 20 may be oscillated, for example using piezoelectric crystals (not shown). O-ring 19 isolates the chamber 18 from the remainder of the ultrasonic handpiece 10.

The ultrasonic handpiece 10 allows for fluid flow through the eye during ophthalmic surgery. During such a procedure, the tip attached to the ultrasonic handpiece 10 is inserted through an incision in the eye. Fluid is driven through the irrigation line 14, to the channel 16 and into the chamber 18. The direction of fluid flow is shown by arrows in FIG. 1. The fluid travels out of the chamber 18 into the eye near the tip of the horn 20. The fluid may be used to remove cataractous lenses from the eye utilizing a surgical technique called Phacoemulsification.

Although the conventional ultrasonic handpiece 10 functions, there are drawbacks. The interior of the eye is desired to be kept stable during the ophthalmic procedure. Disturbances in the fluid flow from the handpiece 10 into the eye are undesirable. One such disturbance may be caused by bubbles in the fluid. When these bubbles enter the eye, the bubbles could cause fluctuations in the intra ocular pressure in the eye and can lead to instability in the anterior chamber of the eye. The bubbles may also adversely affect visualization of the operating field. To reduce or eliminate the bubbles, the operator hand primes the ultrasonic handpiece 10. Priming the handpiece 10 includes orienting the ultrasonic handpiece 10 so that the horn 20 is vertical (ninety degrees counterclockwise from the orientation shown in FIG. 1) and tapping the ultrasonic handpiece 10 while fluid is flowing through the chamber 18. Failure of the operator to prime the handpiece 10 may result in the flow disturbances described above. The manufacturer of the ultrasonic handpiece 10 is unable to guarantee that the operator correctly primes the ultrasonic handpiece 10 each time the handpiece 10 is used. For the above reasons, it may be challenging to ensure that the ultrasonic handpiece 10 provides uniform intra ocular pressure.

BRIEF SUMMARY OF THE INVENTION

A method and system provide a surgical handpiece including a housing and a horn. The housing has a retrograde channel and a chamber therein. The retrograde channel connects an irrigation line and the chamber. The horn is held within the housing such that a portion of the horn resides within the chamber.

DETAILED DESCRIPTION OF THE PREFERRED EMBODIMENTS

The exemplary embodiments relate to surgical handpieces, such as ultrasonic handpieces, used in surgeries including ophthalmic surgery. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system provide a surgical handpiece including a housing and a horn. The housing has a retrograde channel and a chamber therein. The retrograde channel connects an irrigation line and the chamber. The horn is held within the housing such that a portion of the horn resides within the chamber.

Figure 2A:
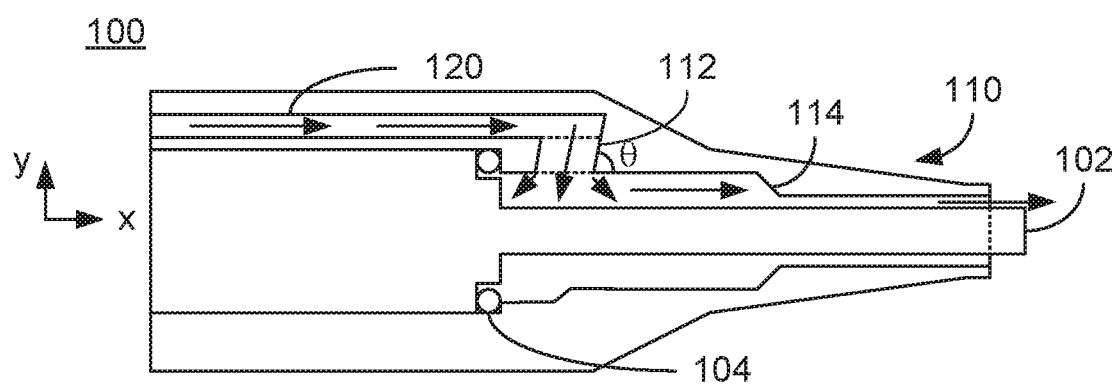
FIG. 2A depicts a cross sectional side view of an exemplary embodiment of a surgical handpiece.
Figure 2B:
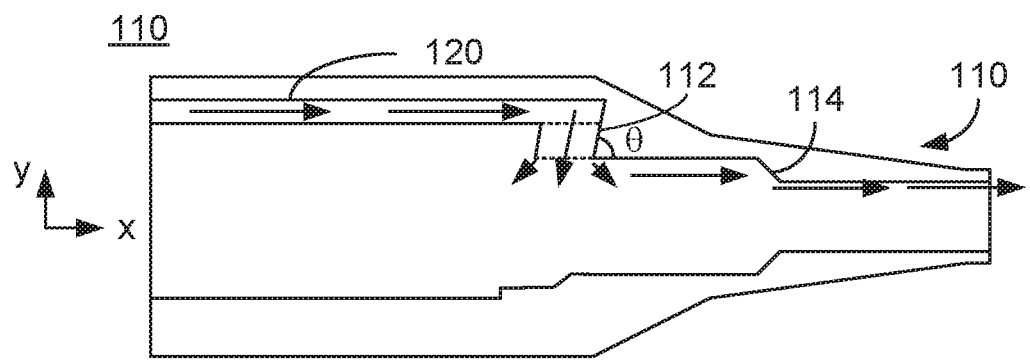
FIG. 2B depicts a cross sectional side view of a housing of an exemplary embodiment of a surgical handpiece.
Figure 2C:
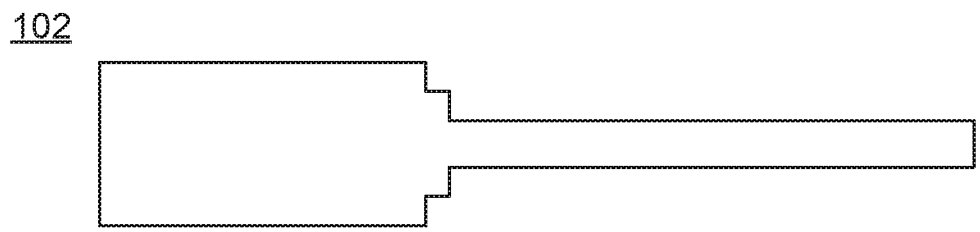
FIG. 2C depicts a cross sectional side view of a horn of an exemplary embodiment of a surgical handpiece.

FIGS. 2A, 2B and 2C depict a side view of an exemplary embodiment of a surgical handpiece 100 usable in ophthalmic surgery and the surgical handpiece components. The surgical handpiece 100 may be an ultrasonic handpiece. However, the surgical handpiece 100 may be another type of surgical handpiece capable of flowing fluid to an operating site such as the eye. The surgical handpiece 100 includes a housing 110 and a horn 102. The horn 102 may be an ultrasonic horn coupled with piezoelectric crystals or other means for oscillating the horn 102. Alternatively, the horn 102 may have another function. Other components of the surgical handpiece 100 are not shown for simplicity.

The housing 110 includes a retrograde channel 112 and a chamber 114. Also shown is an irrigation line 120. In the embodiment shown, the irrigation line 120 is integrated into the housing 110. In such embodiments, the irrigation line 120, retrograde channel 112 and chamber 114 form a continuous channel or space in which fluid may flow. However, in other embodiments, the irrigation line 120 is within a separate component connectable to the housing 110. Thus a dashed line indicates that the irrigation line 120 may be separated from the retrograde channel 112.

The chamber 114 may be centrally located in the housing 110. The horn 102 fits within the chamber 114 and may be isolated by o-ring 104 or other mechanism that prevents fluid from leaking from the chamber 114. The remaining space between the walls of the chamber 114 and the horn 102 allow fluid to flow through the chamber 114 and out near the tip of the horn 102. In the example of FIG. 2A, fluid exits housing 110 in the space between chamber 110 and horn 102 near the distal end of horn 102. The distal end of horn 102 is generally cylindrical in shape as is the distal end of housing 110. As such, fluid may flow from chamber 114 through the cylindrical space formed between horn 102 and the interior surface of housing 110, and to the surgical site. The chamber 114 has sections with different diameters. More specifically, the chamber 114 is reduced in size closer to the distal end of the horn 102 (to the right in FIGS. 2A-2C). During use, a tip or other accessory (not shown) is attached to the distal end of the horn 102. In addition, the handpiece may be connected with other apparatuses for use in surgery. For example, an aspiration line along the axis of the handpiece 100 might be present for removing tissue and/or fluid from the operating field. In FIG. 2A and FIG. 2B, the arrows inside of housing 110 show the direction of fluid flow The retrograde channel 112 connects the irrigation line 120 with the chamber 114. The channel 112 is termed a retrograde channel because the walls of the channel are at an angle, θ, with the x-direction. The angle θ is nonzero and acute. The x-direction is the direction of the axis of the horn 102 and chamber 114. The positive x-direction may also be seen as the direction of fluid flow through the irrigation line 120 and through the chamber 114. The angle θ may be at least ten degrees and not more than eighty degrees. In some embodiments, angle θ is at least thirty degrees and not more than sixty degrees. In some such embodiments, the angle θ is at least forty degrees and not more than fifty degrees. For example, the angle θ may be nominally forty-five degrees. Thus, the inlet to retrograde channel 112 from the irrigation line 120 is closer to the front (positive/larger values of x) of the housing 110, while the outlet of the channel 112 to the chamber 114 is closer to the back (negative/smaller values of x) of the housing 110.

The retrograde nature of the channel 112 may also be seen with respect to fluid flow through the retrograde channel 112. The arrows in FIGS. 2A and 2B indicate the direction of fluid flow through the irrigation line 120, the retrograde channel 112 and the chamber 114. Fluid flows primarily in the positive x-direction in the irrigation line 120 and chamber 114. In the retrograde channel 112, however, fluid flows generally along the axis of the retrograde channel 112. For example, if the angle θ is forty-five degrees, the velocity components in the negative x-direction and negative y-direction within the retrograde channel 112 may be substantially equal. The velocity of fluid in the retrograde channel 112 thus has a nonzero component in the negative x-direction. This direction is opposite to the general direction of fluid flow in the irrigation line 120 and chamber 114. Flow through the retrograde channel 112 is thus at least partially in the reverse direction.

At the outlet of the retrograde channel 112, the flow expands radially outward into the chamber 114 in an expansion jet. This expansion jet has nonzero velocity components in both the positive x-direction and the negative x-direction. The expansion jet also has nonzero velocity components in the negative y-direction (perpendicular to the general direction of fluid flow in the chamber 114 and irrigation line 120). Because the retrograde channel 112 is at the angle θ from the x-direction, the expansion jet has a larger velocity component in the negative x-direction than a channel at a right angle or obtuse angle from the positive x-direction. Consequently, fluid flowing from the retrograde channel 112 into the chamber 114 is more likely to fill the back of the chamber 114 in a region near the o-ring 104. The chamber 114 may be fully backfilled and air between the retrograde chamber 112 and o-ring 104 may be better removed by an initial flow of fluid through the handpiece.

Figure 1:
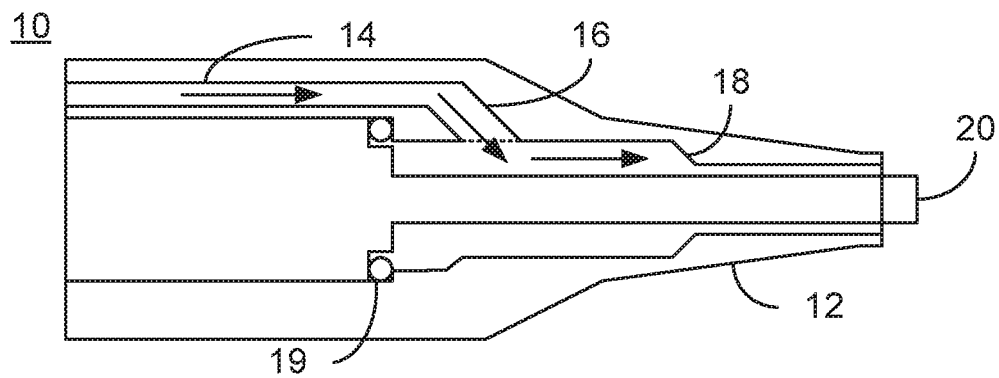
FIG. 1 depicts a portion of a conventional ultrasonic handpiece.

The surgical handpiece 100 may have improved operation. Referring to FIG. 1, it has been determined that a source of bubbles in the conventional surgical handpiece 10 is air that may become trapped between the channel 16 and the o-ring 19. As discussed above, these bubbles may cause flow disturbances that can adversely affect the surgical procedure being performed. Consequently, the conventional surgical handpiece 10 is carefully hand-primed by the operator.

In contrast, the surgical handpiece 100 of FIGS. 2A-2C is automatically primed due to the configuration of the housing 110 and the resulting reverse flow of fluid in the chamber 114. To automatically prime the surgical handpiece 100, fluid is simply flowed through the handpiece 100. Because of the retrograde channel 112, the expansion jet of fluid flowing into the chamber 114 has a significant nonzero velocity component in the negative x-direction. This feature of the retrograde channel 112 in combination with a smaller size of at least part of the chamber 114 allows fluid in the expansion jet to fill the space between the o-ring 104 and the outlet of the retrograde channel 112. Although side views only are shown in FIGS. 2A-2C, the fluid may fill the entire space within the chamber 114 behind the channel 112. The flow of fluid may force air/other gases that might otherwise become trapped in the chamber 114 toward the tip of the handpiece 100 (i.e. to the right) and out of the chamber 114. In some embodiments, the air/gas is removed from the chamber irrespective of the orientation of the surgical handpiece 100. For example, the surgical handpiece 100 may be oriented as shown in FIGS. 2A-2C or oriented with its tip down (rotated ninety degrees clockwise) but still have air/gas removed from the chamber 114 by the flow of fluid during priming. Thus, the surgical handpiece 100 need not be rotated counterclockwise to have its tip vertical and tapped while fluid flows or otherwise hand-primed by the operator. Instead, the configuration of the retrograde channel 112 and chamber 120 allow for backfilling of the chamber 114 by the flow of fluid and, therefore, improved priming of the surgical handpiece 100.

The priming may be further improved by shaping the chamber 114 to reduce flow anomalies. For example, the diameter of the chamber 114 between the retrograde channel 112 and distal end of the horn 102 may be reduced to eliminate recirculation zones. Recirculation zones may allow bubbles forced out of the region between the retrograde channel 112 and the o-ring 104 to become trapped further down the chamber 114. Reducing such recirculation zones may make removal of bubbles more likely and improve priming of the surgical handpiece 100. The precise dimensions of sections of the channel 114, the dimensions and angle θ of the retrograde channel 112, and velocity of the fluid may be tailored for specific applications. Generally, the reduced diameter portion of horn 102 downstream from the o-ring 104 (i.e. to the right of the o-ring 104 in FIG. 2A) is cylindrical. Likewise, chamber 114 is cylindrical and surrounds the reduced diameter portion of horn 102.

Because the surgical handpiece 100 is automatically primed, the operator need not be relied upon to hand-prime (i.e. tap) the surgical handpiece. Disturbances in the flow of fluid from the handpiece to the eye or other surgical field may be more reliably reduced or eliminated by the configuration of the housing 110. Consequently, performance of the surgical handpiece 100 may be improved and the ability of a surgeon to perform procedures may be improved.

Figure 3A:
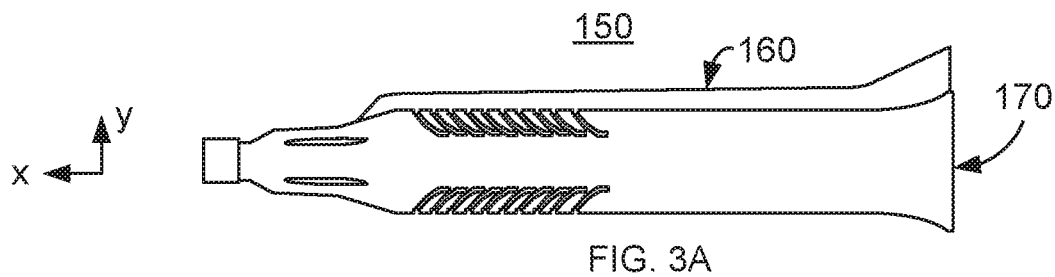
FIG. 3A depicts a side view of an exemplary embodiment of a surgical handpiece.
Figure 3B:
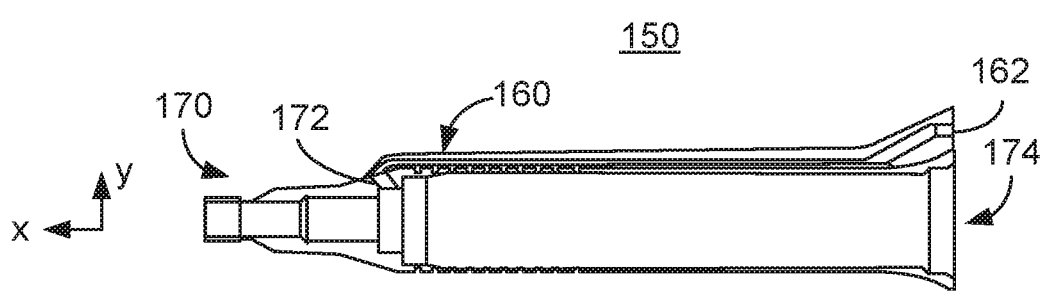
FIG. 3B depicts a cross-sectional side view of an exemplary embodiment of a surgical handpiece.
Figure 3C:
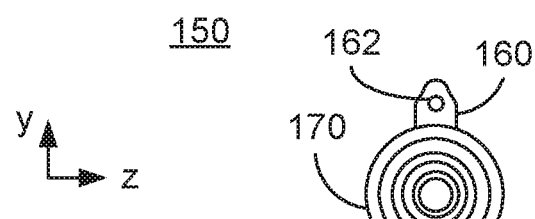
FIG. 3C depicts a cross sectional end view of an exemplary embodiment of a surgical handpiece.
Figure 3D:
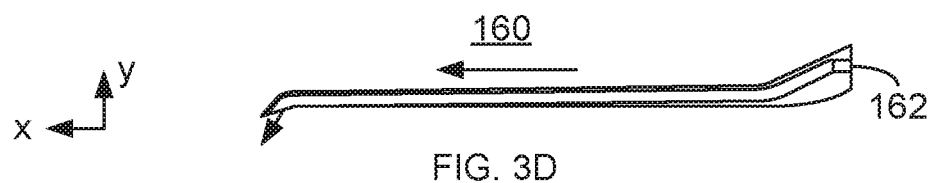
FIG. 3D depicts a cross-sectional side view an exemplary embodiment of the irrigation piece of a surgical handpiece.
Figure 3E:
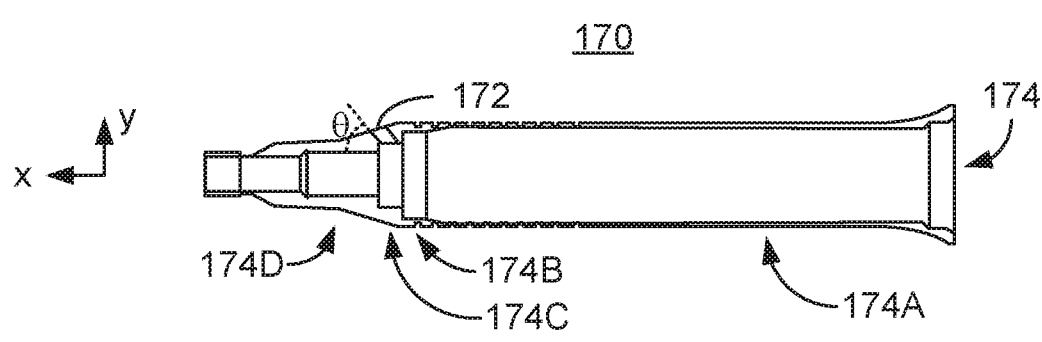
FIG. 3E depicts a cross-sectional side view of an exemplary embodiment of the housing of a surgical handpiece.
Figure 3F:
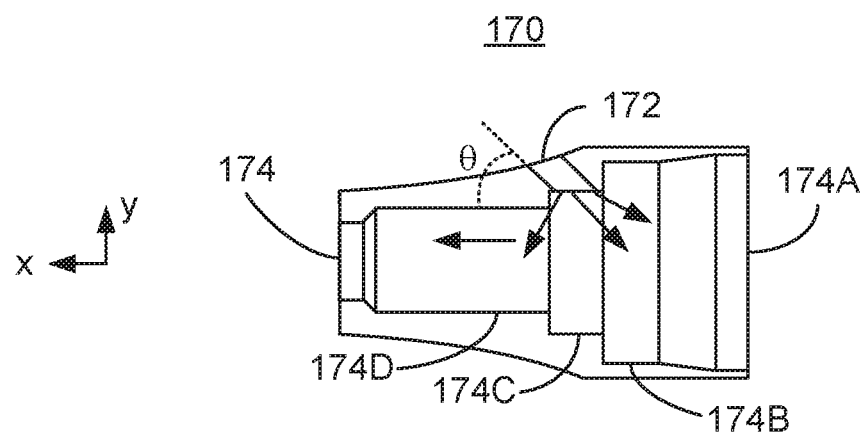
FIG. 3F depicts a detailed cross-sectional side view of an exemplary embodiment of a portion of the housing of a surgical handpiece.

FIGS. 3A, 3B, 3C, 3D, 3E, and 3F depict various views of an exemplary embodiment of a surgical handpiece 150 usable in ophthalmic surgery and the surgical handpiece components. The surgical handpiece 150 includes an irrigation piece or irrigation channel 160 and a housing 170. FIGS. 3A and 3B depict a side view and a cross-sectional side view of the surgical handpiece 150. FIG. 3C depicts a cross sectional end view of the surgical handpiece 150. FIG. 3D depicts a cross-sectional side view of the irrigation piece 160. FIG. 3E depicts a cross-sectional side view of the housing 170. FIG. 3F depicts a detailed cross-sectional side view of a portion of the housing 170. The surgical handpiece 150 may be an ultrasonic handpiece. However, the surgical handpiece 150 may be another type of surgical handpiece capable of flowing fluid to the operating field. The surgical handpiece 150 may also include a horn, which is not shown in FIGS. 3A-3F. Such a horn may be an ultrasonic horn or may have another function. As discussed above, a tip or other accessory that is inserted into the eye during use of the surgical handpiece 150 may be coupled with the distal end of the handpiece 150 (to the left in FIGS. 3A, 3B, and 3E). Other apparatuses including but not limited to an aspiration line might be coupled with the handpiece 150. Other components of the surgical handpiece 150 are not shown for simplicity. The handpiece 150 is analogous to the handpiece 100.

The irrigation piece 160 includes an irrigation line 162 through which fluid may flow. The direction of fluid flow through the irrigation line 162 is shown by the arrows in FIG. 3D. In the embodiment shown, the irrigation piece 160 is a separate component that may be attached to the housing 170. In other embodiments, the irrigation line 162 may be integrated into the housing 170. Thus, irrigation line 162 is analogous to the irrigation line 120.

The housing 170 includes a retrograde channel 172 and a chamber 174. The housing 170, retrograde channel 172 and chamber 174 are analogous to the housing 110, retrograde channel 112 and chamber 114, respectively. The chamber 174 may be centrally located in the housing 170. A horn (not shown) fits within the chamber 174 and may be isolated by an o-ring or other mechanism that prevents fluid from leaking from the chamber 174.

The retrograde channel 172 connects the irrigation line 162 with the chamber 174. The retrograde channel 112 is at a nonzero, acute angle, θ, with the x-direction. The angle θ is shown in FIGS. 3E and 3F. The angle θ may be at least ten degrees and not more than eighty degrees. In some embodiments, angle θ is at least thirty degrees and not more than sixty degrees. In some such embodiments, the angle θ is at least forty degrees and not more than fifty degrees. For example, the angle θ may be nominally forty-five degrees. Thus, the inlet to retrograde channel 172 from the irrigation line 162 is closer to the front (positive/larger values of x) of the housing 170, while the outlet of the channel 172 to the chamber 174 is closer to the back (negative/smaller values of x) of the housing 170.

The fluid flow through the retrograde channel 172 may be understood with reference to the arrows in FIG. 3F. The velocity of the fluid flow in the retrograde channel 172 has a nonzero component in the negative x-direction. Stated differently, fluid flow in the retrograde channel 172 is at least partially in a reverse direction, opposite to the general direction of fluid flow in the irrigation line 162 and chamber 174. At the outlet of the retrograde channel 172/inlet into the chamber 174, the flow expands outward into the chamber 174 in an expansion jet. This expansion jet has nonzero velocity components in both the positive and negative x-directions.

The chamber 174 also includes sections 174A, 174B, 174C and 174D. The sections 174A, 174B, 174C and 174D have decreasing diameter. The diameter of section 174D may be sufficiently small that recirculation zones may be reduced or eliminated from the chamber 174. As a result, bubbles forced out of the region behind the retrograde channel 172 may be less likely to become trapped further down the chamber 174 (i.e. in the x-direction in chamber 174). The diameter of the section 174A and configuration of the retrograde channel 112 are also such that the chamber 174 is backfilled during priming. The precise dimensions of sections 174A, 174B, 174C and 174D of the channel 174, the dimensions and angle θ of the retrograde channel 172, and velocity of the fluid may be tailored for specific applications.

The surgical handpiece 150 may have improved operation. The surgical handpiece 150 is automatically primed due simply by flowing fluid through the handpiece 150. Because of the orientation of the retrograde channel 172 and the configuration of the chamber 174, the expansion jet of fluid flowing into the chamber 174 more completely backfills the chamber 174. The fluid may substantially fill the entire space within the chamber 174 behind the channel 172. Air/other gases that might otherwise become trapped in the chamber 174 may be forced toward the tip of the handpiece 150 and out of the chamber 174 by the fluid flow. In some embodiments, the air/gas is removed from the chamber irrespective of the orientation of the surgical handpiece 150. Improved priming of the surgical handpiece 150 is achieved.

Because the surgical handpiece 150 is automatically primed, the operator need not be relied upon to hand-prime (i.e. tap) the surgical handpiece 150 while the surgical handpiece 150 is in a specific orientation. Disturbances in the flow of fluid from the handpiece 150 to the eye or other surgical field may be more reliably reduced or eliminated. Consequently, performance of the surgical handpiece 150 may be improved and the ability of a surgeon to perform procedures may be enhanced.

Figure 4:
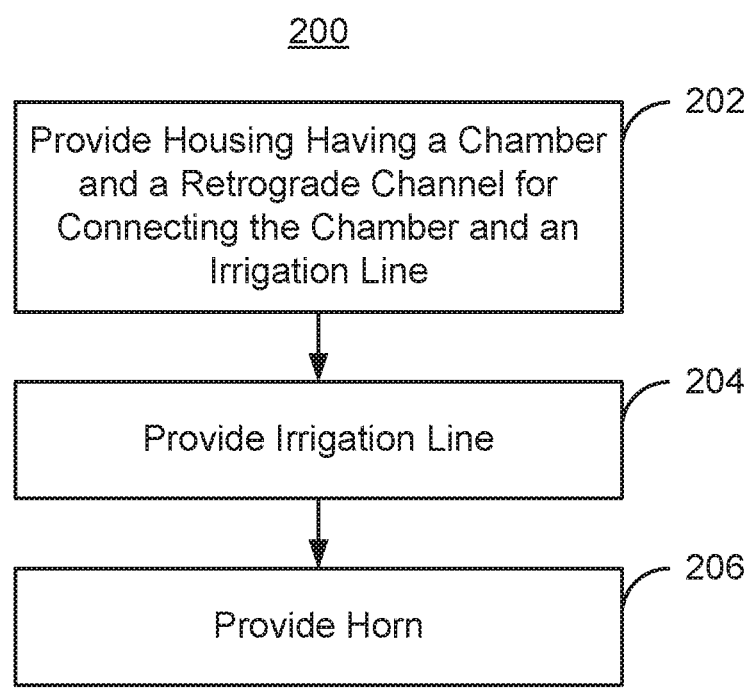
FIG. 4 is a flow chart depicting an exemplary embodiment of a method for providing a surgical handpiece.

FIG. 4 is an exemplary embodiment of a method 200 for providing a surgical handpiece such as the surgical handpiece(s) 100 and/or 150. For simplicity, some steps may be omitted, interleaved, and/or combined. The method 200 is also described in the context of the surgical handpiece 100. However, the method 200 may be used to form the surgical handpiece 150 and/or an analogous surgical handpiece.

The housing 110 having a chamber 114 and retrograde channel 112 is provided, via step 202. The irrigation line 112 is provided, via step 204. In some embodiments, step 204 includes forming the irrigation piece 160 and attaching the irrigation piece 160 to the housing 170. In other embodiments, the irrigation line 120 may be formed by hollowing a portion of the housing 110. Thus, the irrigation line 120 may be integrated into the housing 110 or the irrigation line 162 may be separable from the housing 170 in a manner analogous to the surgical handpiece 150.

The horn 102 is provided, via step 206. Step 206 may include forming the horn 102 and mounting the horn 102 in the housing 110. For example, the housing 110 and horn 102 may include matching screw threads. Also in step 206, the o-ring 104 may be put in place.

Using the method 200, the surgical handpiece 100 and/or 150 may be fabricated. Thus, the benefits of one or more of the surgical handpieces 100 and/or 150 may be achieved.

A method and system for providing a surgical handpiece have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

What is claimed is:

1. A surgical handpiece comprising:
   an irrigation line terminating at a retrograde channel;
   a housing having a chamber therein, the retrograde channel connecting the irrigation line to the chamber;
   wherein the retrograde channel is at an acute angle with respect to an axis of irrigation flow through the irrigation line at the end of the irrigation line coupled to the retrograde channel.

2. The surgical handpiece of claim 1 wherein the acute angle is at least ten degrees and not more than eighty degrees.

3. The surgical handpiece of claim 2 wherein the acute angle is at least thirty degrees and not more than sixty degrees.

4. The surgical handpiece of claim 2 wherein the acute angle is at least forty degrees and not more than fifty degrees.

5. The surgical handpiece of claim 1 wherein the housing includes a front and a back, the chamber being closer to the front than the back and wherein the retrograde channel has an inlet and an outlet, the inlet being closer to the front than the outlet.

6. The surgical handpiece of claim 1 wherein the chamber has a plurality of sections having a plurality of diameters.

7. The surgical handpiece of claim 1 wherein the retrograde channel has an inlet and an outlet, the outlet being connected to the chamber, an expansion jet of fluid from the outlet completely filling the chamber.

8. The surgical handpiece of claim 1 wherein the irrigation line is integrated into the housing.

9. The surgical handpiece of claim 1 wherein the irrigation line is coupled with the housing.

10. The surgical handpiece of claim 1 wherein the horn is an ultrasonic horn.

11. An ultrasonic surgical handpiece comprising:
    an irrigation line;
    a housing having a fluid flow axis, a retrograde channel and a chamber therein, the retrograde channel connecting the irrigation line and the chamber, the retrograde channel having a channel axis at an angle with the fluid flow axis, the angle being at least thirty degrees and not more than sixty degrees with respect to the fluid flow axis at the end of the irrigation line coupled to the retrograde channel;
    an ultrasonic horn held within the housing, a portion of the ultrasonic horn residing in the chamber.

* * * * *